(12) United States Patent
Olalde Rangel

(10) Patent No.: US 7,553,501 B2
(45) Date of Patent: Jun. 30, 2009

(54) IMMUNE PHYTO-NEUTRACEUTICAL COMPOSITION

(75) Inventor: Jose Angel Olalde Rangel, 519 Cleveland St., Suite 101, Clearwater, FL (US) 33755

(73) Assignee: Jose Angel Olalde Rangel, Clearwater, FL (US)

( * ) Notice: Subject to any disclaimer, the term of this patent is extended or adjusted under 35 U.S.C. 154(b) by 0 days.

(21) Appl. No.: 11/420,516

(22) Filed: Nov. 16, 2006

(65) Prior Publication Data

US 2008/0118582 A1    May 22, 2008

(51) Int. Cl.
*A61K 36/00* (2006.01)
*A61K 36/25* (2006.01)
*A61K 36/254* (2006.01)
*A61K 36/074* (2006.01)
*A61K 36/28* (2006.01)

(52) U.S. Cl. ............... 424/725; 424/728; 424/195.15; 424/737; 424/767

(58) Field of Classification Search ............ None
See application file for complete search history.

(56) References Cited

U.S. PATENT DOCUMENTS 5,744,187 A * 4/1998 Gaynor .................. 426/599
6,551,627 B1 * 4/2003 Yoon et al. ............. 424/725
2003/0083242 A1 * 5/2003 Galdes et al. ............ 514/12

OTHER PUBLICATIONS

Mylonakis et al. Plasma Viral Load Testing inthe Management of HIV Infection; American Family Physician, Kansas city, Feb. 1, 2001, vol. 63, Iss. 3 pp. 1-6.*
HIV/AIDS Monitoring; Improved HIV Viral Load Test Approved by FDA; Blood Weekly, Atlanta Sep. 26, 2002, pp. 1-2.*
Animal Models (HBVO; Trimera Disease Model Developed for Hepatitis B: Cancerweekly Plus; Atlanta; Feb. 1999 pp. 1-2.*
Davis, G. Treatment of Chronic Hepatitis C; British Medical Journal; Nov. 2001 pp. 1-3.*
Phillipson, J. New Drugs From Nature—It Could Be Yew; Phytotherapy Research 13 (1999) pp. 2-8.*
Revilla et al. Comparison of Several Procedures Used for the Extraction of Anthocynains From Red Grapes; J. Agric. Food Chem. 1998, 46, pp. 4592-4597.*

* cited by examiner

*Primary Examiner*—Patricia Leith

(57) ABSTRACT

Phytoceutical composition for the prevention and treatment of inmune disorders. A specific combination of extracts of plants is taught, as well as the formulations based on categorizing plants into one of three groups, Energy, Bio-Intelligence and Organization.

1 Claim, No Drawings

IMMUNE PHYTO-NEUTRACEUTICAL COMPOSITION

PRIOR RELATED APPLICATIONS

Not applicable.

FEDERALLY SPONSORED RESEARCH STATEMENT

Not applicable.

REFERENCE TO MICROFICHE APPENDIX

Not applicable.

FIELD OF THE INVENTION

The invention relates to a phytoceutical formulation used to treat immune related diseases. The formulation is a particular combination of plants and has a synergistic effect in combination.

BACKGROUND OF THE INVENTION

The academic study of medicinal plants for the treatment of diverse diseases has been nearly as pervasive as the study of Western medicines. The active principles from many traditional medicines have been extracted from plants, the curative agents identified and their mechanisms of action determined. Plant based medicines are typically well tolerated, with less severe side effects as well as a smaller range of side effects. In contrast, while synthetic drugs can be highly effective, their use is often hampered by severe side effects. Additionally, while synthetic pharmaceuticals are based upon single chemicals, many phytomedicines exert their beneficial effects through the additive or synergistic action of several chemical compounds acting at single or multiple target sites associated with a physiological process. As pointed out by Tyler (1999), this synergistic or additive pharmacological effect can be beneficial by eliminating the problematic side effects associated with the predominance of a single xenobiotic compound in the body. In this respect, Kaufman et al. (1999) extensively documented how synergistic interactions underlie the effectiveness of a number of phytomedicines. This theme of multiple chemicals acting in an additive or synergistic manner likely has its origin in the functional role of secondary products in promoting plant survival. For example, in the role of secondary products as defense chemicals, a mixture of chemicals having additive or synergistic effects at multiple target sites would not only ensure effectiveness against a wide range of herbivores or pathogens but would also decrease the chances of these organisms developing resistance or adaptive responses (Kaufman et al., 1999; Wink, 1999). Conclusion: On one hand, synthetics may have the required efficacy for disease treatments; however this can be marred by severe side effects. On the other hand, despite the excellent medicinal qualities of many plants, they are individually insufficient to take chronic degenerative diseases into remission. However, there is mounting evidence which demonstrates that medical plants contain synergistic and/or side-effect neutralizing combinations (Gilani and Rahman, 2005). Thus, what is needed in the art is better treatment regimes with improved patient tolerance, while providing sufficient efficacy.

SUMMARY OF THE INVENTION

A number of known beneficial plants were classified according to their capacity to enhance the three main elements that support overall health, in chronic degenerative diseases: Energy (E), Bio-intelligence (I) and Organization (O). A synergistic effect is expected when all three categories of herbs (E, I, O) are included in a formulation.

Thus, on the case of diseases that cause a depression of the immune system, one embodiment of the invention provides an effective, natural composition for treating immune related diseases. The composition can be used alone, or can be combined with simultaneous use of one or more pharmaceutical compositions. It can be used for the treatment of HIV, Cancer, and others.

DETAILED DESCRIPTION OF THE INVENTION

'Pharmaceutically acceptable excipients' is used herein according to art accepted meanings, and includes those ingredients needed to formulate a medicine for mammalian use, including the use of gelatin capsules.

'Synergistic' or 'synergy' is used herein to mean that the effect is more than its additive property. In preferred embodiments, the synergy is at least 1.5, 2, 5, or 10 fold.

By use of 'plants,' what is meant herein is that the plant (or that portion with medicinal activity) is used whole, ground, or as an extract. Also included are purified active ingredients, and derivatives thereof. However, it is believed that the best efficacy of plants used herein is achieved with the use of the entire plant or its extracts, rather than with the use of isolated active ingredients.

Further, although plants are named here according to commonly used nomenclature, with improving taxonomy plants are often reclassified. Whenever a plant is referenced, it includes related species with similar active ingredients.

The following examples are illustrative only, and should not serve to unduly limit the invention.

EXAMPLE 1

Plant Characteristics—Immune Disorders

Energy Enhancing Components.—

*Eleutherococcus* or *Acanthopanax senticosus* (Russian Ginseng, Siberian Ginseng, Eleuthero, Devil's Shrub, Buisson du Diable, Touch-me-not, Wild Pepper, Shigoka, *Acantopanacis senticosus*). Contains terpenoids (oleanolic acid), Eleutheroside A (daucosterol); Eleutheroside B (siringin); Eleutheroside B1 (isofraxidin); Eleutheroside B4 (sesamin); Eleutheroside D and E (heteroside siringoresinol); Eleutheroside C, G, I, K, L and M; phytosterols (β-sitosterol), polysaccharides (eleutherans), volatile oils, caffeic acid, coniferyl aldehyde, and sugars. *Eleutherococcus*, increases energy and vitality levels, improving physical and mental performance, and quality of life. Increases the contribution of oxygen to muscles and allows for longer exercising and faster recovery. Prevents tiredness. The adaptogenic effects of the root of eleutherococcus are produced by metabolic regulation of energy, nucleic acids, and tisular proteins. Eleuthero improves the formation of glucose-6-phosphate. The glucose-6-phosphate oxidizes by the way of pentose, producing substrates for the biosynthesis of nucleic acids and proteins. On the other hand, it increases the activity of succhinate dehydrogenase and of muscular malato dehydrogenase, enzymes that intervene in the cycle of tricarboxylic acids, generating ATP. The eleutherosids B and E are responsible for this adaptogenic activity. Eleuthero has been shown to bind to gluco or mineralocorticoid receptors, and stimulate production of T-lymphocyte and natural killer cells (immune-stimulant activity). It has antioxidant activity as well as. Russian Ginseng contains at least 40 active ingredients.

*Panax ginseng* (Chinese ginseng, panax, ren shen, jintsam, ninjin, Asiatic ginseng, Japanese ginseng, Oriental ginseng, Korean red ginseng) The main active components are ginsenosides (protopanaxadiols and protopanaxatriols types) these have been shown to have a variety of beneficial effects, including anti-inflammatory, antioxidant, and anticancer effects. They also confer energizing properties because they increase ATP synthesis. Results of clinical research studies demonstrate that *Panax* may improve immune function. For example, ginsenoside RH2 induces apoptosis via activation of caspase-1 and caspase-3 and upregulation of Bax in human neuroblastoma. Also, diets containing ginseng, decreased/modulated the numbers of aberrant fossi. Thus, this herbal supplement may exert significant and potentially beneficial effects on decreasing the amount of precancerous lesions and inducing apoptosis. Studies indicate that *Panax* enhances phagocytosis, NK lymphocytes cell activity, and the production of interferon; improves physical and mental performance in mice and rats; and increases resistance to exogenous stress factors. The incorporation of this phytomedicine provides at least 86 active principles in a single therapeutic.

*Panax quinquefolius* (American Ginseng, Anchi, Canadian Ginseng, Five Fingers, Ginseng, American, North American Ginseng, Red Berry, Ren Shen, and Tienchi) is related to *Panax ginseng*, but is a distinct species with higher levels of ginsenoside Rb1 and without ginsenoside Rf. These substances confer energizing properties because they increase ATP synthesis. Ginsenoside Rb1 is believed to limit or prevent the growth of new blood vessels, making it useful to treat tumors. It has antioxidant, anti-inflammatory, and hypolipidemic effects. Studies revealed that quinquefolius and estradiol equivalently induced RNA expression of pS2. *Panax*, in contrast to estradiol, caused a dose-dependent decrease in cell proliferation. Quinquefolius had no adverse effect on the cell cycle while estradiol significantly increased the proliferative phase (percent S-phase) and decreased the resting phase -G(0)-G(1) phase. Concurrent use of quinquefolius and breast cancer therapeutic agents resulted in a significant suppression of tumoral cell growth for most drugs evaluated. The incorporation of this phytomedicine provides at least 206 active principles in a single therapeutic.

*Pfaffia paniculata* (Suma, Brazilian Ginseng, Pfaffia, Para Tudo, Corango-acui, *Hebanthe paniculata, Gomphrena paniculata, G. eriantha, Iresine erianthos, I. paniculata, I. tenuis, P. eriantha, Xeraea paniculata*) contains active glycosides (beta-ecdysone and three ecdysteroids), six different pfaffic acids, phytosterols (sitosterol and stigmasterol) and triterpene glycosides. *Pfaffia* contains up to 11% Saponins (triterpene glycosides), which two derived products have received patents in Japan as antineoplasic compositions. Its germanium content probably accounts for its properties as an oxygenator at the cellular level, and its high iron content may account for its traditional use for anemia. This herb increases energy through an increase in ATP synthesis and oxygenation at the cellular level, and it also has anabolic activity at the muscular level. Incorporation of this phytomedicine provides at least 44 active principles in a single therapeutic.

*Rhodiola rosea* (Golden Root, Roseroot, Artic root) consists mainly of phenylpropanoids (rosavin, rosin, rosarin—all specific to *R. rosea*), phenylethanol derivatives (salidroside, rhodioloside, tyrosol), flavanoids (catechins, proanthocyanidins, rodiolin, rodionin, rodiosin, acetylrodalgin, tricin), monoterpenes (rosiridol, rosaridin), triterpenes (daucosterol, beta-sitosterol), and phenolic acids (chlorogenic, caffeic, hydroxycinnamic and gallic acid). There are many species of *Rhodiola*, but rosavins seem to be unique to *R. Rosea*, and it is the preferred species for this formulation. *Rhodiola* increases energy levels because it activates ATP synthesis and re-synthesis in mitochondria, stimulating reparative processes after intense exercise. In a recent study two extracts elaborated from *Rhodiola* (gossypetin-7-O-L-rhamnopyranoside and rhodioflavonoside) were examined, displaying activity against a prostate cancer cell line and showing inhibitory activity against *Staphylococcus aureus*. Another study demonstrated that *Rhodiola* extract has cytostatic and antiproliferative effect, this last raises hope for its use in anticancer therapy by enhancing effectiveness of cytostatics. Incorporation of this phytomedicine provides at least 28 active principles in a single therapeutic.

*Schizandra chinensis* (*Schisandra spenenthera*, Chinese magnolia vine fruit, also known as Wuweizi and Wurenchum). The major active principles of *Schizandra* are lignans called schizandrines. *Schizandra* increase activities in some enzymes that intervene in the oxidative phosphorylation. It reduces fatigue and increases exercise resistance. P-glycoprotein-mediated drug efflux is one of the major causes of cancer multidrug resistance (MDR). A recent study found that Schisandrin B reversed the drug resistance of four MDR cell lines characterized with overexpression of P-glycoprotein and fully restored the intracellular drug accumulation by interacting with P-glycoprotein. Schisandrin B has a core structure of dibenzocyclooctadiene, representing a novel P-glycoprotein inhibitor. Also, another study revealed that Sch B is able to inhibit the proliferation of human hepatoma cells and induce apoptosis, which goes through Caspase-3-dependent and Caspase-9-independent pathway accompanied with the down-regulation of Hsp70 protein expression at an early event. This plant provides at least 81 active principles in a single therapeutic.

Bio-Intelligence Modulators.—

*Andrographis paniculata* (King of Bitters, Kalmegh, Quasabhuva, The Creat and Kirayat) Primary active principles associated with Andrographis (AG) are: flavonoids, glucosides and diterpenic lactones (andrographolides). As evidenced in various clinical studies, these substances offer immuno-modulator and anti-inflammatory properties. Studies also suggest that they stimulate the immune systems and activate macrophages. A recent study demonstrated morphological and biochemical changes in andrographolide-induced cell death in human prostatic adenocarcinoma PC-3 cells. Andrographolides bring about anti cancer activity by blocking the cell cycle at the G0-G1 phase through the induction of the cell cycle inhibitor, p27, and the concomitant decrease in Cdk4 levels. Also, an even more recent study revealed that Andrographolide, an extract from Andrographis paniculata might act as a chemosensitizer when co-administered with 5-fluorouracil, adriamycin and cisplatin, and the mechanism of reversal modulation of multidrug resistance by AG in HCT-8/5-FU (multidrug-resistant cancer cell line) might be related to its downregulation of overexpression of P-170. This plant offers at least 11 active principles in a single therapeutic.

*Astragalus membranaceus* (Huang-Qi, Huangqi) This plant contains three main types of active principles. Isoflavones, which act as anti-oxidants; astragalans which act as immune-stimulants and anti-inflammatory by stimulating the phagocytic activity of macrophages, of the cytotoxic response of T and NK lymphocytes and of the production and activity of interferon; and astragalosides which act as modulators of the hypothalamus-hypofisis-adrenal axis response. It also conveys antioxidative properties. Huang-qi, a traditional Chinese medicine, has been used to ameliorate side effects of cancer chemotherapy in China. Its effects inducing cell differentiation and cell death, in K562 and HEL cells, have been shown in a recent study. This plant offers at least 38 active principles in a single therapeutic.

*Coriolus versicolor* (Kawara take, Yun zhi, turkey tail) Among the active principles isolated from the mycelia of Chinese Medicinal fungus *Coriolus versicolor* is the polysaccharide peptide (PSP) which has proven its benefits in many clinical trials in China and Japan. The cell death process of the anti-cancer agent PSP in human promyelocytic leukemia HL-60 cells and citotoxicity of PSP on normal human T-lymphocytes has also been evaluated. PSP induces apoptosis in human promyelocytic leukemia HL-60 cells but not on the T-lymphocytes. The apoptotic machinery induced by PSP was linked with a Bcl-2/bax ratio reduction, a drop in mitochondrial transmembrane potential, cytochrome c release, and caspase-3, -8 and -9 activation. Thus, the development of PSP as a novel anticancer agent is supported by a selective behavior inducing apoptosis in cancerous cells while respecting normal cells. Another active principle of *Coriolus* is protein bound polysaccharide Krestin (PSK). There are various studies to support its anti-cancer activity. However, in a significant more recent meta-analysis of data, from more than 1000 patients, outcomes for standard chemotherapy were compared with those for chemotherapy plus PSK Results of this study suggested that adjuvant chemotherapy with PSK can improve both survival and disease-free survival of patients with curatively resected colorectal cancer. Other recent studies also validate this poslysacharide's cancer adjuvant property, such as: metastatic submandibular lymphnode treated successfully with palliative oral (5-FU+PSK) chemotherapy in the elderly; effects of PSK on T and dendritic cells differentiation in gastric or colorectal cancer patients; Protein-bound polysaccharide K induced apoptosis of human Burkitt lymphoma cell line.

*Echinacea* spp. (*E. angustifolia, E. purpurea*, Black Sampson, Purple Coneflower, Rudbeckia, Missouri Snakeroot, Red Sunflower) contains alkaloids (Isotussilagine, tussilagine), amides (echinacein, isobutylamides), carbohydrates (echinacin, polysaccharides (heteroxylan and arabinogalactan), inulin, fructose, glucose, pentose), glycosides (echinacoside), terpenoids (Germacrane), Cichoric acid, betaine, methylpara-hydroxycinnamate, vanillin, phytosterols, and volatile oils. Echinacea has been the subject of hundreds of clinical and scientific studies which have primarily used an extract of the root and aerial portions of the botanical. The rich content of polysaccharides and phytosterols in *Echinacea* are what make it a strong immune system stimulant. The sesquiterpene esters also have immuno-stimulatory effects. Echinacin has also been found to possess anti-fungal and antibiotic properties. This component of *Echinacea* also has cortisone-like actions which can help promote the healing of wounds and helps to control the inflammatory reactions. Results from a very recent in vivo study have shown that daily consumption of *Echinacea* is indeed prophylactic, extends life span, significantly abates leukemia and extends life span of leukemic mice. The incorporation of this phytomedicine into compositions provides at least 70 active principles in a single therapeutic.

*Ganoderma lucidum* (Reishi, also *G. tsugae, G. valesiacum, G. oregonense, G. resinaceum, G. pfezfferi, G. oerstedli*, and *G. ahmadii*) is an edible fungus containing bitter triterpenoids (ganoderic acid), β-D-glucan, coumarins, alkaloids and ergosterols. The main active principles of this mushroom are sterols and beta-proteoglucans which bestow anti-inflammatory and immune-modulating properties, because they increase the phagocytotic capacity of macrophages, and increase the production—and lifetime—of CD4 lymphocytes as well. Treatment with beta-glucan may be beneficial for cancer patients with or at risk for metastasis. The beta-glucan-dependent signaling pathways are critical for our understanding of anticancer events and development of cancer therapeutic agents. The polysaccharide component with a branched (1->6)-beta-D-glucan moiety of *G. lucidum* (PS-G) has been reported to exert anti-tumor activity and activation of natural killer cells. Also data suggests that PS-G can effectively promote the activation and maturation of immature dendritic cells suggesting that PS-G may posses a potential in regulating immune responses. *Ganoderma* contains at least 32 active principles.

*Grifola frondosa* (Maitake, Dancing Mushroom; also *G. sordulenta, Polyporus umbellatus* and *Meripilus giganteus*) contains the primary polysaccharide, β-D-glucan in the 1.3 and 1.6 forms. It also contains alpha glucan, lipids, phospholipids, and ergosterol. β-D-glucan is recognized as an effective immuno-stimulator. This substance increases the activity of macrophages and other immunocompetent cells that destroy tumor cells. The substance also improves the immunological efficiency of these cells by increasing production of cytokines IL-1, IL-2 and others. The final result is an increase of the defenses against infectious and tumoral diseases. Also, D-Fraction, a polysaccharide extracted from maitake mushrooms (*Grifola frondosa*), has been reported to exhibit an antitumor effect through activation of immunocompetent cells, including macrophages and T cells, with modulation of the balance between T-helper 1 and 2 cells. Study results suggest that D-Fraction can decrease the effective dosage in tumor-bearing mice by increasing the proliferation, differentiation, and activation of immunocompetent cells and thus provide a potential clinical benefit for patients with cancer. Use of *Grifola* has demonstrated to diminish side effects of chemotherapy in test conducted in animals. The incorporation of this phytomedicine provides at least 6 active ingredients for therapeutic use.

*Hydrastis canadensis* (golden seal, yellow root, turmeric root) contains mainly isoquinoline alkaloids (xanthopuccine, berberine, hidrastine, hidrastanine, beta-hydrastine, canadine and canadaline). These confer anti-inflammatory, bacteriostatic, and bacteriocidal, and effects. In general, its antibacterial action is directed to microbes' metabolic inhibition, inhibition of the formation of enterotoxins, and inhibition of bacterial adhesion. Berberine inhibits activating protein 1 (AP-1), a key factor in transcription of the inflammation. It also exerts a significant inhibitory effect on lymphocyte transformation, so its anti-inflammatory action seems to be due to the inhibition of DNA synthesis in the activated lymphocytes or to the inhibition of the liberation of arachidonic acid from the phospholipids of the cellular membrane. It also has immuno-modulating properties by increasing production of immunoglobulins G and M and stimulating the phagocytotic capacity of macrophages. A recent study shows Berberine antiproliferative activity in vitro and induction of apoptosis/necrosis of the U937 human tumour cell line and murine melanoma B16 cell line growing in vitro. Also, Berberine has been shown to inhibit arylamine N-acetyltransferase activity and gene expression in mouse leukemia L 1210 cells. This plant provides at least 34 active principles for therapeutic use.

*Lentinus edodes* (Hua gu, Shiitake, Shiitake mushroom) Lentinan, obtained from the Shiitake mushroom is a β1-3, β1-6 δ-glucan. Glucan preparations are always heterogeneous in molecular weight but Lentinan is particularly big, in the order of 400,000-1.000.000 daltons. Clinical studies have demonstrated that it extends survival in gastric and colon-rectum cancer patients. Studies also show that lentinan boosts the immune system. Thus, the active principles are mostly present as glucans of different glycoside links, such as (1->3), (1->6)-beta-glucans y (1->3)-alpha-glucans and as true heteroglicanes. They act as immune modulators due to the increase in concentration of humoral mediators, such as: TNF-α, gamma interferon, Interleukin-2, Interleukin-6, and the production of NO and activity of catalase, in macrophages and T lymphocytes. They also increase the citotoxicity of NK cells and macrophages. Another active principle obtained from *Lentinus* is AHCC (Active Hexose Correlated Compound). This compound offers immune-modulating and anti-neoplasic activity. Increasing survival rate as well as a significant reduction in transaminase levels and certain seric tumor markers. To be noted are also an improvement in Lymphocyte and erythrocyte count, anemia and appetite. Also, the anti-tumor activity of the polysaccharide L-II—isolated from the fruiting body of *Lentinus*—on mice-transplanted sarcoma 180 was mediated by immunomodulation in inducing T-cells and macrophage-dependent immune system responses. Addition of Lentinan to chemotherapy in inoperable advanced gastric cancer showed higher efficacy regardless of pathological alterations; higher and sustained improvement in QoL was also observed.

*Morinda citrifolia* (Noni, Indian Mulberry, Ba Ji Tian, Nono, Nonu, Fruta de Queso and Nhau) Many of its components have been identified among them: Several acids, vitamins (A & C), potassium, anthraquinones, fitosterols, flavonolglicosides, aucubine, alizarine, Noni encompasses at least 23 active principles, 5 vitamins and 3 minerals. Studies have proven the inhibition of angiogenic initiation and disruption of newly established human vascular networks by noni. An immunomodulatory polysaccharide-rich substance (Noni-ppt) from the fruit juice of *Morinda citrifolia* has been found to possess both prophylactic and therapeutic potentials against the immunomodulator sensitive Sarcoma 180 tumour system. The antitumour activity of Noni-ppt produced a cure rate of 25%-45% in allogeneic mice and its activity was completely abolished by the concomitant administration of specific inhibitors of macrophages (2-chloroadenosine), T cells (cyclosporine) or natural killer (NK) cells (anti-asialo GM1 antibody). Noni-ppt showed synergistic or additive beneficial effects when combined with a broad spectrum of chemotherapeutic drugs, including cisplatin, adriamycin, mitomycin-C, bleomycin, etoposide, 5-fluorouracil, vincristine or camptothecin. Noni was also effective in reducing the growth rate and proliferation of newly developing capillary sprouts, thus demonstrating its anti-angiogenesic properties.

*Petiveria alliacea* (Anamú, Apacin, Apacina, Apazote De Zorro, Aposin, Ave, Aveterinaryte, Calauchin, Chasser Vermine, Congo Root, Douvant-douvant, Emeruaiuma, Garlic Guinea Henweed, Guine, Guinea, Guinea hen leaf, Gully Root, Herbe Aux Poules, Hierba De Las Gallinitas, Huevo De Gato, Kojo Root, Kuan, Kudjuruk, Lemtewei, Lemuru, Mal Pouri, Mapurit, Mapurite, Mucura-caa, Mucura, Mucuracaa, Ocano, Payche, Pipi, Tipi, Verbena Hedionda, Verveine Puante, Zorrillo) contains Allantoin, Arborinol, Arborinoliso Astilbin, Benzaldehyde, Benzoic-acid Benzyl-2-hydroxy-5-ethyl-trisulfide, Coumarin, Dibenzyl Trisulfide, Engeletin, alpha Friedelinol, Isoarborinol, Isoarborinol-acetate, Isoarborinol-cinnamate, Isothiocyanates, Kno3, Leridal, Leridol, Leridol-5-methyl Ether, Lignoceric Acid, Lignoceryl Alcohol, Lignoceryl Lignocerate, Linoleic Acid Myricitrin, Nonadecanoic Acid, Oleic Acid, Palmitic Acid, Pinitol, Polyphenols, Proline,trans-n-methyl-4-methoxy, Senfol, β-Sitosterol, Stearic Acid, Tannins, and Trithiolaniacine. Its therapeutic activities include anti-inflammatory, immune-stimulant and antimicrobial effects. This phytomedicine provides about 25 active principles.

*Sutherlandia frutescens* (Cancer Bush, also *Sutherlandia Microphylla*) contains L-canavanine, pinitol, GABA (gamma aminobuteric acid), and asparagine. In addition, a novel triterpenoid glucoside known as 'SU1' has been isolated and characterized. The therapeutic indications include anti-inflammatory, antioxidant, and immuno-modulador. Selective anti-tumoral effects: a) Alteration of proteins production: Inhibits the transport of L-arginine through the membranes and competes for its incorporation in cellular proteins. L-Cannavanine, instead of arginine, is incorporated in the new polypeptic chains by action of the arginyl-tRNA synthase. This situation results in the production of canavanyl proteins, structurally evil, that alter critical reactions of the metabolism of DNA and RNA and the synthesis of other proteins. b) Stimulates the apoptosis of tumor cells, inducing the activation of caspase-3, the degradation of poly(ADP-ribose) polymerase (PARP) and the apoptotic fragmentation of DNA, regulating the expression of Bcl-2 and Bcl-xI genes. c) Cytostatic effect on tumor cells: Produces the detention of the mitosis in its G1 and G2/M phases. d) Assists antineoplasic treatment: Increases the sensibility of tumor cells to radiotherapy and to chemotherapeutical agents, such as doxorubicin, cysplatin, 5-fluorouracil, mitoxantrone and bleomicine. This phytomedicine provide at least 5 active principles.

*Tabebuia avellanedae* (Pau d'arco, Ipê, Lapacho, Tahuari, Taheebo, Trumpet Tree, Tabebuia Ipê, Tajy; also *T. ipe, T. nicaraguensis, T. schunkeuigoi, T. serratifolia, T. altissima, T. palmeri, T. impetiginosa, T. heptaphylla, Gelseminum avellanedae, Handroanthus avellanedae, H. impetiginosus, Tecoma adenophylla, Tec. avellanedae, Tec. eximia, Tec. impetiginosa, Tec. integra, Tec. ipe*) extracts contain diverse quinone derivatives and a small quantity of benzenoids and flavonoids, including beta-lapachone, xyloidone, tabebuin, quercetin, tecomine, and steroidal saponins. One important ingredient is lapachol, a derivative of which was patented in 1975. It has anti-inflammatory and antibacterial effects Recent studies on the effect of beta-lapachone, a quinone obtained from the bark of this tree, are sheding new light into the possible molecular mechanism of its anti-cancer activity. Beta-lapacone's action increases apoptosis associated with a decrease in bcl-2 and expression, an increase of BAX, and an activation of caspase-3 and caspase-9, inhibiting the growth of A549 human lung carcinoma cells. Beta-lapachone also suppresses human prostate cancer cell growth via down regulation of pRB phosphorylation and induction of Cdk inhibitor p21 (WAF1/CIP1). Another example is beta-lapachone's down-regulation of cyclooxygenase-2 and telomerase activity in human prostate carcinoma cells. The incorporation of this phytomedicine into a composition provides at least 32 active principles in a single therapeutic.

*Uncaria tomentosa* (Cat's Claw, Peruvian Cat's Claw, Samento, Saventaro, Uña de Gato, also *Uncaria guianensis*) has several alkaloids including pentacyclic oxindole alkaloids (POA) (isomitraphylline, isopteropodine, mitraphylline, pteropodine, speciophylline, uncarine F), tetracyclic oxindole alkaloids (TOA) (isorynchophylline, rynchophylline), glycosides (triterpenic quinovic acid glycosides), hirsutine, tannins, catechins, phytosterols (beta-sitosterol, campesterol, stigmasterol), triterpenes, polyphenols, flavanols and oligomeric proanthocyanidins (OPC). It is an immune-stimulant, an anti-inflammatory, vasodilator, and antioxidant. Also, cat's claw has shown in vitro anticancer activity in a recent study. *U. tomentosa* extracts and fractions exert, in addition to antimutagenic activity, a direct antiproliferative activity on MCF7, a human breast cancer line. Another study points out at the induction of apoptosis and inhibition of proliferation in human tumor cells K562 and HL60 when treated with *U. tomentosa*. This phytomedicine provides at least 29 active ingredients.

*Vitex agnus castus* (Chaste Tree or chaste berry) The most important active principles are an essential oil, two iridoid glycosides (aucubine and agnuside); a flavone (casticin, which seems to be the primary active principle) and 3 minor flavonoids derived from kaempferol and quercetin. A recent study has shown G2-M arrest and antimitotic activity mediated by casticin.

Organizational Improvers.—

Fulvic Acid (FA): Deals with a mixture of low molecular weight components among which are uronic acid, glucosides and amino acids. The biologic activity of fulvic acid is uniquely determined by the functional groups of its molecules (carboxyls, hydroxiphenyls, tioles, hydro-quinone, amino and imido groups). Fulvic acid (FA) is resistant to microbial degradation. Fulvic acid accelerates oxidative phosphorylation and protein synthesis. Antitumoral and antioxidative effects: FA protects the cellular membrane of the action of free radicals and heavy metals. It can scavenge and eliminate free radicals because of its weak acid properties. It can combine with heavy metals and body toxins, removing them form the system. It increases the activity of enzymatic antioxidant systems such as superoxide dismutase. Anti-inflammatory: FA is a powerful anti-inflammatory. Reduces edema by 77%, minimizing pain. Its anti-oxidative properties also help prevent inflammation. FA increases the citotoxic activity of macrophages as well as the synthesis of Interferon and other substances that inhibit the growth of tumoral cells. Increases the phagocytic activity of macrophages, the mechanism being similar to that produced by IL-4.

*Hydrocotile asiatica* (Gotu Kola, Bramhi, Pennywort, Marsh Penny, Pennywort and *Centella asiatica*) contains terpenoids (asiaticoside, brahmoside and brahminoside), aglycones (saponin glycosides), asiaticentoic acid, centellic acid, centoic acid and madecassic acid, sesquiterpenes (caryophyllene, trans-B-farnesene), volatile oils (Germacrene D), alkaloids (hydrocotylin), flavonoids (Quercetin, kaempferol), phytosterols (stigmasterol and sitosterol), and vallerine, fatty acids, resin, and tannins. Asiatic acid (AA) -a pentacyclic triterpene contained in Hydrocoltile induced apoptosis in HT-29 cells via caspase-3 activation. Simultaneous treatment or sequential exposure first to AA and then to CPT-11 (anticancer drug irinotecan hydrochloride) showed an additive effect. Synergism was observed when cells were first exposed to CPT-11 and then to AA. These results suggest that AA can be used as an agent for increasing sensitivity of colon cancer cells to treatment with CPT-11 or as an agent for reducing adverse effects of CPT-11. Also, AA has proven to induce apoptosis in SK-MEL-2 human melanoma cells, and induces apoptosis and cell cycle arrest through activation of extra cellular signal-regulated kinase and p38 mitogen-activated protein kinase pathways in human breat cancer cells. Incorporation of this *Hydrocotile* in a composition provides at least 59 active principles in a single therapeutic.

*Opuntia ficus indica* (Indian Fig, Nopal, Cactus pear, prickly pear) fruit contains vitamin C and characteristic betalain pigments, which radical-scavenging properties and antioxidant activities have been shown in vitro. It also contains vitamins (A, B1, B2, B3,) carotenoids, betaxanthins, tannins, 17 amino acids (of which 7 are essential) and minerals. From the stems and fruits of prickly pear cactus, eight flavonoids, kaempferol, quercetin, kaempferol 3-methyl ether, quercetin 3-methyl ether, narcissin, (+)-dihydrokaempferol (aromadendrin, (+)-dihydroquercetin (taxifolin), eriodictyol, and two terpenoids have been identified. Several studies have demonstrated that *Opuntia* produces a chemical substance which accelerates the synthesis of Heat Shock Proteins (HSP) in response to aggressor agent's impacts, while at the same time they reduce the consumption of these proteins. Thus they improve the protective, reparative and recuperative cellular mechanisms, increasing cell survival and minimizing organ and tissular damage. This is particularly important in cancer patients. HSP proteins also participate in the immune responses, acting as macrophage and other immune-competent cells inductors which participate in the innate immune mechanisms, thus contributing to the immunological system. This phytomedicine incorporates at least 80 active principles in a single therapeutic.

Shark cartilage This natural compound inhibits the proliferation of endothelial cells, competitively blocking the Endothelial Growth Factor at the receptor level. It also inhibits tyrosine EGF and EGF-2 dependant phosphorylation as well as the increase of FCE induced permeability. Shark cartilage also induces endothelial cell apoptosis, by inducing caspase 3, 8 and 9 activation, and the liberation of cytochrome c from the mitochondria to the cytoplasm. Shark cartilage also induces fibrinolitic activity by increasing the secretion, activity and affinity of Tissue Plasminogen Activator (tPA) for endothelial cells. It also inhibits extra cellular matrix degradation, by inhibiting matrix metalloproteinase MMP-2, MMP-7, MMP-9, MMP-12 and MMP-13. It also stimulates angeostatin production. AE 941 a shark cartilage extract, inhibits angiogenesis by blocking the two main pathways that contribute to the process of angiogenesis, matrix metalloproteases and the vascular endothelial growth factor signalling pathway. This is very important in cancer treatment as well as with diseases related with increased angiogenesis.

EXAMPLE 2

Composition-Immune Disorders

A particularly preferred composition is shown in Table 1. Ratios reflect concentration of active ingredient over the natural state. Amounts provided are mg of extract. Obviously, the amount should be increased where the strength is reduced, and vice versa.

TABLE 1

| Active Agent | Ratio | Amount (mg) |
|---|---|---|
| Herbaria | | |
| Energy enhancers | | |
| *Eleutherococcus senticosus* root extract | 5:1 | 20 |
| *Panax ginseng* root extract | 5:1 | 13 |
| *Panax quinquefolius* | 4:1 | 17 |
| *Pfaffia paniculada* root extract | 4:1 | 34 |
| *Rhodiola rosea* root extract | 5:1 | 7 |
| *Schizandra chinensis* | 5:1 | 7 |

TABLE 1-continued

| Herbaria | | |
|---|---|---|
| Active Agent | Ratio | Amount (mg) |
| Bio-Intelligence modulators | | |
| Andrographis paniculata | 5:1 | 34 |
| Astragalus membranaceus root extract | 5:1 | 34 |
| Coriolus versicolor | 10:1 | 27 |
| Echinacea angustifolia root | 6:1 | 13 |
| Echinacea purpurea root | 6:1 | 13 |
| Ganoderma lucidum mushroom extract | 6:1 | 40 |
| Grifola frondosa mushroom extract | 10:1 | 20 |
| Hydrastis canadensis root extract | 5:1 | 13 |
| Lentinus edodes | 4:1 | 40 |
| Morinda citrifolia | 5:1 | 13 |
| Petiveria alliacea | 1:1 | 34 |
| PSK | 1:1 | 13.5 |
| PSP | 1:1 | 13.5 |
| Sutherlandia frutescens extract | 1:1 | 67 |
| Tabebuia avellanedae | 4:1 | 40 |
| Uncaria tomentosa | 4:1 | 40 |
| Vitex agnus castus | 5:1 | 17 |
| Organization improvers | | |
| Fulvic acid | 3:4 | 13 |
| Hydrocotile asiatica | 5:1 | 20 |
| Opuntia ficus indica | 5:1 | 7 |
| Shark cartilage | 4:1 | 40 |
| Total | | 650 |

EXAMPLE 3

A Clinical Study of Formulation's Effectiveness and Tolerance

A study was undertaken to evaluate the effects of the therapeutic formula object of this patent—and formulated under the precepts herein included—in seventy patients with Prostate Cancer—fifteen of which were terminal. Method: A retrospective, multicenter, descriptive, two year long study, where patients were divided in two groups. Group I, consisting of 55 cancer patients stages A to D1 (Whitmore-Jewett); and Group II, including only terminal cancer patients—15 cases—(stage D2 Whitmore-Jewett). Results: Urinary symptoms improved in 96.3% of symptomatic patients (52 improved out of 54 symptomatic cases present in both groups). Bone symptoms improved in 84.6% of the affected symptomatic patients in terminal stage (11 improved out of 13 symptomatic cases, in group II). Prostatic Specific Antigen (PSA) decreased by 86.7% in patients in Group I ($p<0.0004$); while PSA values diminished in 89.1% of patients in Group II ($p<0.05$). Quality of Life improved in 94.5% and 80% respectively in Groups I and II. Conclusions: Results suggest that the therapeutic formula employed, demonstrated to be effective in all stages of this pathology. Tolerance results were outstanding. Only one patient referred side effects—cefalea. However, this condition did not warrant suspension of treatment. Tolerability was 93.3%. Preliminary results on this population strongly suggest that this therapy may offer unexpectedly superior comparative benefits to terminal cancer patients—when contrasted to traditional therapies.

EXAMPLE 4

Principles for Selecting Synergistic Combinations

In order to expand the range of formulations encompassed by the invention, we have categorized beneficial plants into one of three groups, each of which should be present for synergistic effect. The classifications are Energy, Bio-Intelligence and Organization. Plants classified under Energy are associated with ATP synthesis (such as the Krebs cycle, oxidative phosphorylation, beta-oxidation, etc.). Plants classified under Bio-Intelligence are those that regulate the neuroendocrine and immunological systems and cellular processes, thus controlling the interactions between the various systems in the body. Finally, plants classified under Organization are those that relate to the structure and function of specific organs. Combinations of plants from these three classification groups have synergistic effect because they address each necessary component for total health—in effect they provide the triangle on which healing is fully supported.

According to the previous numeral the inclusion of plants for this formulation is given in figure below.

An illustrative example of synergy in medicinal plants is an in vitro study that demonstrates how the activity of herbal Berberine alkaloids is strongly potentiated by the action of 5'-methoxyhydnocarpin (5'-MHC)—an active principle of another phytomedicine (denominated Hydnocarpus wightiana). It shows a strong increase of accumulation of berberine in the cells in the presence of 5'-MHC, indicating that this plant compound effectively disabled the bacterial resistance mechanism against the berberine antimicrobial, thus showing the synergy of both substances. Stermitz F R, et al., Synergy in a medicinal plant: antimicrobial action of berberine potentiated by 5'-methoxyhydnocarpin, a multidrug pump inhibitor. Proc Natl Acad Sci USA. 2000 Feb. 15; 97(4):1433-7.

It may further de demonstrated synergistic effect on a molecular scale by studying the gene expression profile changes in response to various plant ingredients and combinations thereof. Experiments are already underway demonstrating the expression profile in response to the formulations. We will be aided in this work because researchers have already begun studying the expression profiles of various medicinal plants, thus providing a database of knowledge from which to build. E.g., Liu L, et al., Effects of Si-Jun-Zi decoction polisacharides on cell migration and gene expression in wounded rat intestinal ephithelial cells. 2005 January; 93(1):21-9; and Gohil, et al., mRNA Expression Profile of a Human Cancer Cell Line in Response to *Ginkgo Biloba* Extract: Induction de Antioxidant Response and the Golgi System, Free Radic Res. Dic. 2001; 33(6):831-849.

It may also be possible to add tests of plants' combinations for further demonstration of synergistic effects by using experimental models.

What is claimed is:

1. A phyto-nutraceutical composition comprising: *Andrographis paniculata* 34 mg, *Astragalus membranaceus* root extract 34 mg, *Coriolus versicolor* 27 mg, *Echinacea angustifolia* root 13 mg, *Echinacea purpurea* root 13 mg, *Eleutherococcus senticosus* root extract 20 mg, Fulvic acid 13 mg, *Ganoderma lucidum* extract 40 mg, *Grifola frondosa* extract 20 mg, *Hydrastis canadensis* root extract 13 mg, *Hydrocotile asiatica* 20 mg, *Lentinus edodes* 40 mg, *Morinda citrifolia* 13 mg, *Opuntia ficus indica* 7 mg, *Panax ginseng* root extract 13 mg, *Panax quinquefolius* 17 mg, *Petiveria alliacea* 34 mg, *Pfaffia paniculata* root extract 34 mg, Polysaccharide Krestin (PSK) 13.5 mg, Polisaccharopeptide (PSP) 13.5 mg, *Rhodiola rosea* root extract 7 mg, Shark cartilage 40 mg, *Schizandra chinensis* 7 mg, *Sutherlandia frutescens* extract 67 mg, *Tabebuia avellanedae* 40 mg, *Uncaria tomentosa* 40 mg and *Vitex agnus castus* 17 mg; together with pharmaceutically acceptable excipients.

* * * * *